US00PP14365P29

(12) United States Plant Patent
Jensen

(10) Patent No.: US PP14,365 P2
(45) Date of Patent: Dec. 16, 2003

(54) MINIATURE ROSE PLANT 'JENINDI'

(50) Latin Name: *Rosa hybrid*
Varietal Denomination: JENindi

(76) Inventor: Svend Jensen, Kongensgade 32, Christiansfeld 6070 (DK)

( * ) Notice: Subject to any disclaimer, the term of this patent is extended or adjusted under 35 U.S.C. 154(b) by 0 days.

(21) Appl. No.: 10/279,198

(22) Filed: Oct. 25, 2002

(51) Int. Cl.[7] ..... A01H 5/00

(52) U.S. Cl. ..... Plt./121
(58) Field of Search ..... Plt./121

*Primary Examiner*—Bruce R. Campell
*Assistant Examiner*—Annette H. Para

(57) ABSTRACT

A new miniature rose plant which has abundant, orange-red colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Latin name of genus and species: *Rosa hybrid* 'JENindi'.
Variety denomination: The new variety is named 'JENindi'.

BACKGROUND OF THE INVENTION

The present invention constitutes a new and distinct variety of miniature rose plant, which was developed by artificially pollinating an unnamed seedling(not patent in the U.S.) with an unnamed seedling (not patent in the U.S.). The two parents were crossed in the summer of 1999 and the resulting seed was sown in December, 1999 in a controlled glasshouse environment. Out of these seedlings one seedling was selected, as the new variety and named 'JENindi'. The new rose may be distinguished from its seed parent, an unnamed seedling, by the following combination of characteristics:

1. The unnamed seedling has a breeding background in unnamed seedlings.
2. 'JENindi' has medium double flowers, while the unnamed seedling has big single flowers.
3. 'JENindi' has orange-red colored petals, while the unnamed seedling has dark yellow-red petals.

The new variety may distinguished from its pollen parent, an unnamed seedling created by the same inventor, by the following combination of characteristics:

1. The unnamed seedling has a breeding background in unnamed seedlings.
2. 'JENindi' has smaller flowers and foliage as compared to the unnamed seedling.
3. 'JENindi' has orange-red colored petals, while the unnamed seedling has dark pink petals.

BRIEF SUMMARY OF THE INVENTION

Initial asexual reproduction of 'JENindi' by cuttings was first done in Christiansfeld, Denmark. The reproduction was conducted in controlled greenhouse environments. Have here proven to be stabile by propagation with cuttings in several generations. 'JENindi' is a low and compact miniature rose with medium vigor. The shelflife has been tested to be medium.

The objective of the hybridization of this rose variety for commercial greenhouse culture was to create a new and distinct variety with:

1. Uniform and abundant flowers with good keepability;
2. Attractive long lasting foliage and compact growth,
3. Year round flowering under glasshouse conditions;
4. Suitability for production from softwood cuttings in pots.;
5. Durable flowers and foliage which make the variety suitable for distribution in the floral industry.

This combination of qualities was not present in previously available commercial cultivars of this type and distinguish 'JENindi' from all other varieties of which we are aware. The seeds from hybridization were planted in a controlled environment and evaluations were conducted on the resulting plants. 'JENindi' was selected by, Svend Jensen, in his development program in Christiansfeld, Denmark.

BRIEF DESCRIPTIONS OF THE DRAWINGS

Figures 1, 2, 3, 4, 5, 6, 7, 8, 9:
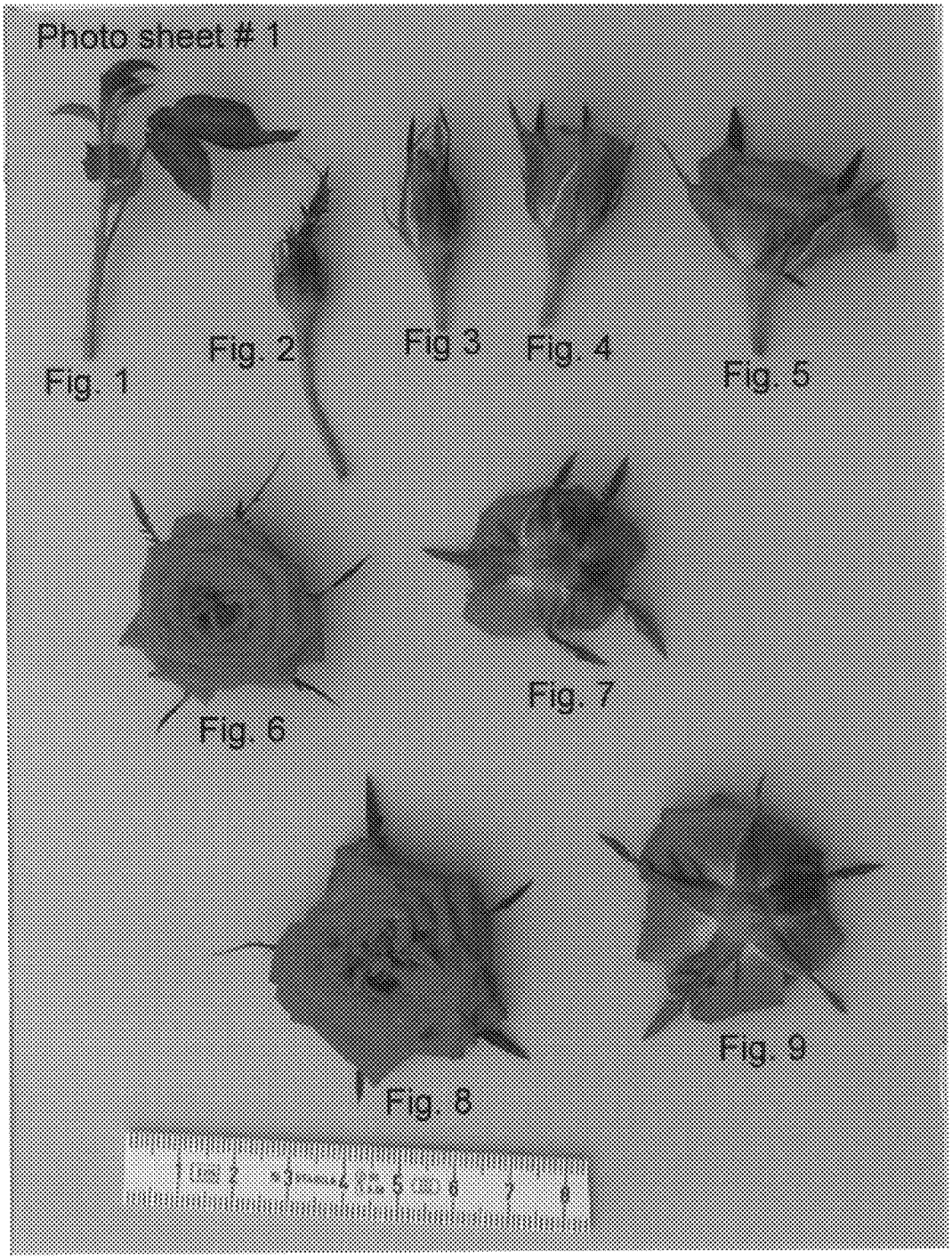

The accompanying color illustrations show as true as is reasonably to obtain in color photographs of this type, the typical characteristics of the buds, flowers, leaves, stems of 'JENindi'. Specifically illustrated in:

Photo sheet # 1:

FIG. 1. Young shoot.
FIG. 2. Bud before opening the sepals.
FIG. 3. Bud at the opening the sepals.
FIG. 4. Bud at the opening the petals.
FIG. 5. Flower during course of opening.
FIG. 6. Open flower—plan view—obverse.
FIG. 7. Open flower—plan view—reverse.
FIG. 8. Fully open flower—plan view—obverse.
FIG. 9. Fully open flower—plan view—reverse.

Figures 10, 11, 12, 13, 14, 15, 16, 17, 18:
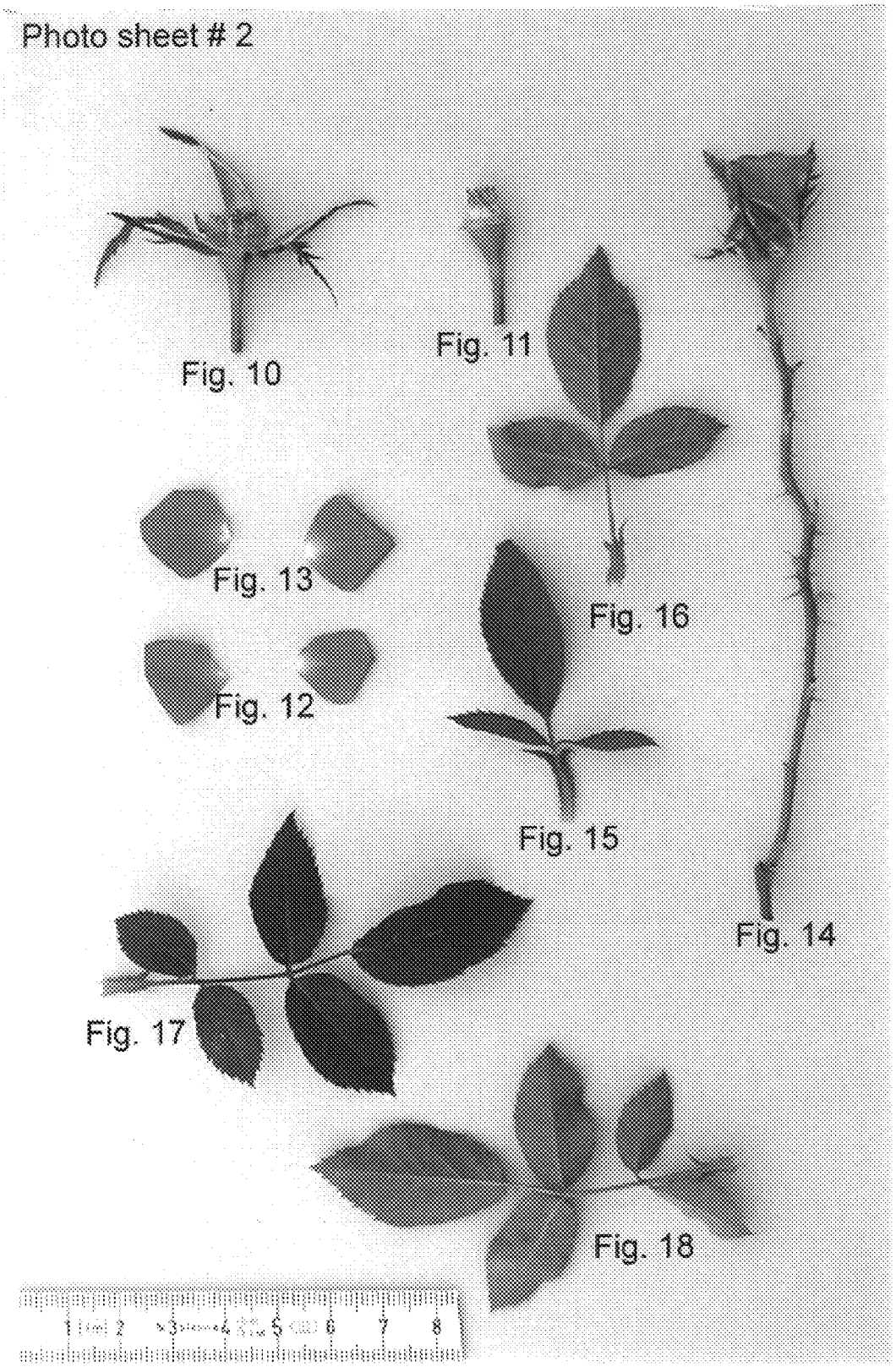

Photo sheet # 2:

FIG. 10. Receptacle showing stamens and pistils.
FIG. 11. Receptacle showing pistils (stamens removed).
FIG. 12. Flower petals, detached—outer surface.
FIG. 13. Flower petals, detached—inner surface.
FIG. 14. Bare stem exhibiting thorns and flower attachment.
FIG. 15. Three leaflets upper side.

FIG. 16. Three leaflets reverse side.

FIG. 17. Five leaflets upper side.

FIG. 18. Five leaflets reverse side.

DETAILED BOTANICAL DESCRIPTION OF THE VARIETY

The following is a detailed description of the Miniature Rose: Rosa hybrid 'JENindi'. The following observations, measurements, values and comparisons describe plants grown in glass houses in Christiansfeld, Denmark. The age of the observed plants where 11 to 13 weeks after propagation by cuttings, and produced as flowering pot plants in container of 10.5 centimeter in diameter. Color references are made using The Royal Horticultural Society (London, England) Colour Chart, 1995, except where common terms of color are used. For a comparison, the nearest existing rose variety is 'POUfiry', a rose variety described and illustrated in U.S. Plant Pat. No. 12,484. Chart 1 details several physical characteristics of 'JENindi' and 'POUfiry'.

CHART 1

| | 'JENindi' | 'POUfiry' |
|---|---|---|
| Petal color, Upper surface | Orange-Red Group 34A | Red Group 40B-C |
| Petal color, Reverse surface | Orange-Red Group 34B | Red Group 41C |
| Petal count | 45–50 | 20–25 |

Parents: Unnamed seedling. Times. Unnamed seedling.

CLASSIFICATION

Botanical: Rosa hybrid.
Commercial: Miniature.

PLANT

Plant growth: Moderately vigorous. Grows compact upright to bushy. When grown as 10 cm pot plant, the average height of the plant itself is 18 to 20 cm, and average with is 20 cm. When grown as a 15 cm pot plant, the average height of the plant itself is 22 to 27 cm, and average with is 30 cm. Production time is generally 11 to 13 weeks depending on average temperature, light level, and cultural practices.

STEM

Color:
*Young wood.*—Yellow-Green Group 146C.
*Older wood.*—Yellow-Green Group 146B.
Thorns:
*Incidence.*—High number of thorns.
*Size.*—3–4 mm.
*Color.*—Greyed-Brown Group 199A.
*Shape.*—Deep concave.
Surface:
*Young wood.*—Smooth.
*Older wood.*—Smooth.
Stem diameter: 2–3 mm.
Internode length: 25–30 mm.
Numbers of internodes: 7–10.

PLANT FOLIAGE

Leaves arranged alternately, compound with three to seven leaflets per leaf, generally symmetrical, abundant, and flat in aspect. Stipules at petiole base.

Quantity of leaves: 7 to 10 per lateral branch.
Leaf size: Medium 75–80 mm(l). times. 50–55 mm(w).
Petioles:
*Color.*—Green Group 137A, with prickles of Greyed-Brown Group 199B. Margins: entire. Length: 10–15 mm. Diameter: about 0,5–1 mm.
Stipules:
*Size.*—6–7 mm. Surface: Smooth. Color: Yellow-Green Group 145C, with intonations of Greyed-Brown Group 199B. Margins: entire.
Rachis:
*Color.*—Yellow-Green Group 148A, with intonations of Greyed-Brown Group 199C. Margins: Margins with stipitate glands. Length: 15 to 25 mm.
Leaflets:
*Edge.*—Serrated.
*Serration.*—Single.
*Shape.*—Ovate with acute apex and obtuse base.
*Texture.*—Smooth.
*Appearance.*—Glossy.
*Size.*—Length: 20 to 30 mm. With: 15 to 20 mm.
*Color.*—Young foliage: Upper surface: Green Group 137B With intonations of Greyed-Orange Group 177 A. Lower surface: Yellow-Green Group 147B.
*Color.*—Mature foliage: Upper surface: Green Group 136A. Lower surface: Yellow-Green Group 147B.

INFLORESCENSE

Blooming habit: Recurrent.
Number of flowers: Generally 1 bud per flowering stem.
Penduncle:
*Color.*—Green Group 139C.
*Texture.*—Smooth, with pubescence and prickles.
*Length.*—30–35 mm.
*Strength.*—Upright.
Receptacle:
*Surface.*—Smooth, glabrous.
*Shape.*—Funnel-shaped.
*Size.*—H: 6–7 mm w: 9–10 mm.
*Color.*—Green Group 138B.
Sepals:
*Quantity.*—5.
*Shape.*—Narrowly Ovate w. acute tip.
*Texture.*—Leathery.
*Margin.*—Foliaceous appendages on 3 of the five sepals.
*Apearance.*—Dull.
*Color.*—Upper surface: Green Group 137C. Reverse surface: Greyed-Green Group 194C.
Buds:
*Size.*—20 mm (h) 20–25 mm (w)upon opening.
*Shape.*—Cupped.
*Color.*—At ¼ opening, Red Group 50A.
Flower:
Duration: As a pot plant, flowers last form 12 to 18 days.
*Fragrance.*—None.
*Size.*—25–40 mm in diameter.
*Form.*—Shape of flower when viewed from the side. Up on opening: Cupped. Open flower: Flat.

*Color.*—Petals, upon opening. Upper surface: Orange-Red Group 34A. Reverse surface: Orange-Red Group 34A.

*Petals after opening.*—Upper surface: Orange-Red Group 34A. Reverse surface: Orange-Red Group 34B.

*Basal petals spots.*—Size: 2–3 mm. Color: White Group 155A.

*General tonality.*—On open flower: Third day: Orange-Red Group 34A. Afterwards: Orange-Red Group 34A.

Petals:

Petal reflex: Outermost petals reflex backwards at opening. Fully open all petals reflex backwards.

Texture: Smooth.

Petal edge: Uniform.

Petal count: Approximately 45–50 on the average per flower.

Petal size:

*Length.*—20 mm.

*With.*—20 mm.

Shape:

*Outer petals.*—Round.

*Inner petals.*—Ovate.

Reproductive organs:

Stamen number: Approximately 80–85 on average per flower.

*Pollen:*

*Color.*—Greyed-Orange Group 164B,

*Abundance.*—Average.

*Anthers.*—Size: 1–2 mm.

*Color.*—Greyed-Orange Group 164B.

*Shape.*—Oblong.

Filaments:

*Size.*—3–4 mm.

*Color.*—Greyed-Orange Group 164C.

Pistils number: Approximately 75–80 on average per flower.

Stigmas:

*Location.*—Lower in location to anthers.

*Color.*—Green-White Group 157B.

Styles:

*Color.*—Greyed-White Group 157B.

*Length.*—2 to 3 mm.

DEVELOPMENT

Vegetation: Dense.

Blooming: Abundant.

Aptitude to bear fruit: Poor.

Resistance to diseases: Above average resistance to mildew and Botrytis under normal growing conditions in Christiansfeld, Denmark. Hips/seeds has not been observed due to that the plant has never been grown to the stage of seed development, due to the fact, that the variety is developed for use as a flowering pot plant only.

Winter hardiness & Drought/heat tolerance: Due to the fact, that this variety is a potted flowering plant, developed for one time use only, the plant is not tested for winter hardiness or drought/heat tolerance.

I claim:

1. A new and distinct variety of rose plant of the miniature class, substantially as herein illustrated and described as a distinct and novel rose variety due to its abundant orange-red flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

Photo sheet # 1

Photo sheet # 2